US 11,666,394 B2

(12) United States Patent
Grover et al.

(10) Patent No.: US 11,666,394 B2
(45) Date of Patent: Jun. 6, 2023

(54) SURGICAL INSTRUMENTS, INSTRUMENT DRIVE UNITS, AND SURGICAL ASSEMBLIES THEREOF

(71) Applicant: Covidien LP, Mansfield, MA (US)

(72) Inventors: Simon R. Grover, Cambridge (GB); Charles F. Kilby, Cambridgeshire (GB); Daniel L. Fuller, Haverhill (GB)

(73) Assignee: COVIDIEN LP, Mansfield, MA (US)

( * ) Notice: Subject to any disclaimer, the term of this patent is extended or adjusted under 35 U.S.C. 154(b) by 567 days.

(21) Appl. No.: 16/882,865

(22) Filed: May 26, 2020

(65) Prior Publication Data

US 2020/0281669 A1 Sep. 10, 2020

Related U.S. Application Data

(62) Division of application No. 15/307,130, filed as application No. PCT/US2015/026057 on Apr. 16, 2015, now Pat. No. 10,687,906.

(Continued)

(51) Int. Cl.
*A61B 34/30* (2016.01)
*A61B 17/34* (2006.01)
(Continued)

(52) U.S. Cl.
CPC .............. *A61B 34/30* (2016.02); *A61B 17/34* (2013.01); *A61B 34/35* (2016.02); *A61B 34/71* (2016.02);
(Continued)

(58) Field of Classification Search
CPC ......... A61B 34/30; A61B 34/35; A61B 34/37; A61B 34/70; A61B 34/71
(Continued)

(56) References Cited

U.S. PATENT DOCUMENTS 5,814,038 A * 9/1998 Jensen .................. A61B 34/30
606/1
5,882,344 A * 3/1999 Stouder, Jr. ........ A61B 17/3417
604/164.11
(Continued)

FOREIGN PATENT DOCUMENTS

WO 2012104785 A1 8/2012
WO 2013159933 A1 10/2013

OTHER PUBLICATIONS

International Search Report for (PCT/US2015/026057) date of completion is Jul. 9, 2015 (5 pages).
(Continued)

*Primary Examiner* — John R Downey
(74) *Attorney, Agent, or Firm* — Carter, Deluca & Farrell, LLP

(57) ABSTRACT

A surgical instrument is configured for coupling with an instrument drive unit that drives an actuation of the surgical instrument and operatively supports the surgical instrument. The surgical instrument includes a housing, an elongate body extending distally from the housing, an end effector extending distally from the elongate body, and a plurality of driven members rotatably disposed within the housing. The plurality of driven members is nested with one another. Each driven member of the plurality of driven members is coupled to a respective cable that is attached to the end effector. The plurality of driven members is configured for engagement with an instrument drive unit.

20 Claims, 12 Drawing Sheets

Related U.S. Application Data

(60) Provisional application No. 61/985,549, filed on Apr. 29, 2014.

(51) Int. Cl.
*A61B 34/00* (2016.01)
*A61B 34/35* (2016.01)
*A61B 17/00* (2006.01)

(52) U.S. Cl.
CPC ..... *A61B 34/74* (2016.02); *A61B 2017/00477* (2013.01); *A61B 2017/3409* (2013.01)

(58) Field of Classification Search
USPC ...................................... 606/1, 130
See application file for complete search history.

(56) References Cited

U.S. PATENT DOCUMENTS

| | | | |
|---|---|---|---|
| 6,828,023 B2 | 12/2004 | Broome et al. | |
| 6,923,613 B2* | 8/2005 | Stuyt | B25J 9/102 414/735 |
| 6,991,627 B2 | 1/2006 | Madhani et al. | |
| 7,204,844 B2* | 4/2007 | Jensen | A61B 34/35 606/205 |
| 9,743,995 B2* | 8/2017 | Lohmeier | A61B 34/71 |
| 9,993,307 B2* | 6/2018 | Lohmeier | B25J 19/0075 |
| 10,687,906 B2 | 6/2020 | Grover et al. | |
| 2005/0187576 A1* | 8/2005 | Whitman | A61B 17/1155 227/176.1 |
| 2005/0228440 A1* | 10/2005 | Brock | A61B 34/30 606/205 |
| 2010/0318101 A1 | 12/2010 | Choi | |
| 2011/0230894 A1* | 9/2011 | Simaan | A61B 1/00183 606/130 |
| 2011/0288573 A1* | 11/2011 | Yates | A61B 50/36 227/175.1 |
| 2012/0239075 A1* | 9/2012 | Widenhouse | A61B 17/1155 606/197 |
| 2013/0123783 A1* | 5/2013 | Marczyk | A61B 18/1445 606/1 |
| 2013/0338433 A1* | 12/2013 | Goldman | A61B 1/0052 600/102 |
| 2014/0175149 A1* | 6/2014 | Smith | A61B 17/1155 227/175.2 |
| 2015/0105798 A1* | 4/2015 | Lohmeier | A61B 34/71 606/130 |
| 2016/0346513 A1* | 12/2016 | Swaney | A61B 17/3417 |
| 2017/0095299 A1* | 4/2017 | Hendrick | A61B 34/30 |

OTHER PUBLICATIONS

European Search Report dated Feb. 22, 2018, corresponding to European Application No. 15785563.6; 7 pages.

* cited by examiner

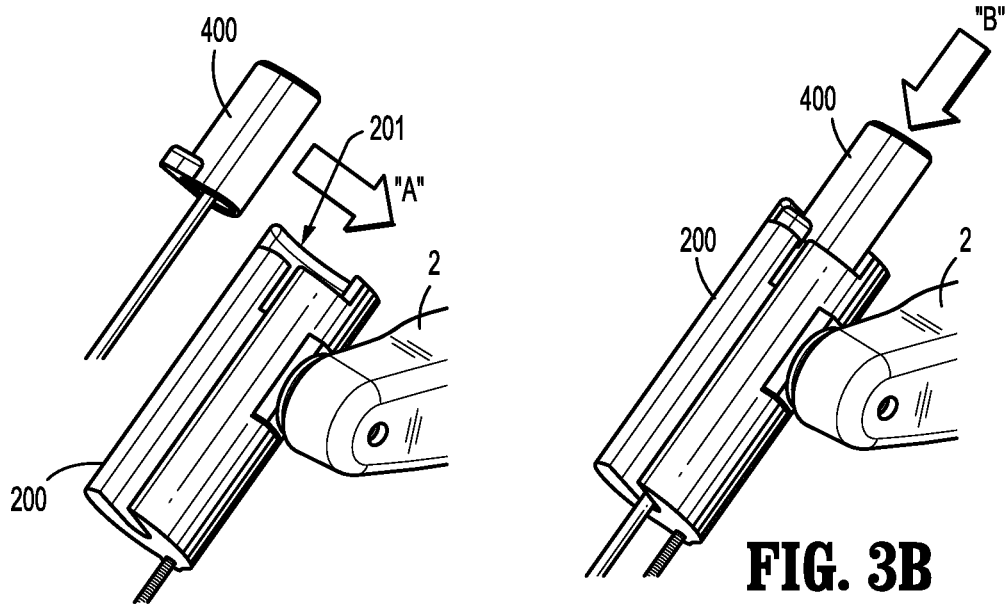
FIG. 3A
FIG. 3B
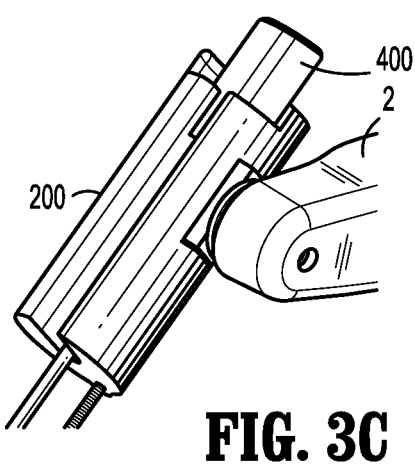
FIG. 3C

SURGICAL INSTRUMENTS, INSTRUMENT DRIVE UNITS, AND SURGICAL ASSEMBLIES THEREOF

CROSS-REFERENCE TO RELATED APPLICATIONS

This application is a Divisional Application of U.S. patent application Ser. No. 15/307,130, filed on Oct. 27, 2016, which is a U.S. National Stage Application filed under 35 U.S.C. § 371(a) of International Patent Application No. PCT/US2015/026057, filed Apr. 16, 2015, which claims the benefit of and priority to U.S. Provisional Patent Application No. 61/985,549, filed Apr. 29, 2014, the entire disclosure of each of which is incorporated by reference herein.

BACKGROUND

Robotic surgical systems have been used in minimally invasive medical procedures. Some robotic surgical systems include a console supporting a robot arm and a surgical instrument or at least one end effector that includes forceps or a grasping tool that is mounted to the robot arm. The robot arm provides mechanical power to the surgical instrument for its operation and movement. Each robot arm may include an instrument drive unit that is operatively connected to the surgical instrument.

Prior to or during use of the robotic system, surgical instruments are selected and connected to the instrument drive units of each robot arm. For proper installation to be completed, certain connecting features of the surgical instrument must be matingly engaged to corresponding connecting features of the instrument drive unit. Once these features are matingly engaged, the instrument drive unit can drive the actuation of the surgical instrument. However, connection and removal of surgical instruments to instrument drive units can be difficult. Further, cables for actuating functions of the surgical instrument can become entangled upon rotation of the surgical instrument relative to the instrument drive unit.

Therefore, there is a need for an instrument drive unit having a minimized size, that allows for greater degrees of freedom for an attached surgical instrument, and that provides for an easier removal and attachment of a surgical instrument.

SUMMARY

In accordance with an aspect of the present disclosure, a surgical assembly is provided. The surgical assembly includes a surgical instrument and an instrument drive unit configured for disposal of the surgical instrument. The surgical instrument has a proximal end portion and a distal end portion. The surgical instrument includes a housing disposed at the proximal end portion, an elongate body extending distally from the housing, an end effector extending distally from the elongate body, and a plurality of driven members rotatably disposed within the housing. The plurality of driven members is nested with one another. Each driven member is coupled to a respective cable that is attached to the end effector Instrument drive unit is configured for driving an actuation of the end effector of the surgical instrument and to operatively support the surgical instrument. The instrument drive unit includes a plurality of actuators nested with one another. Each actuator is configured for engagement with one corresponding driven member. The instrument drive unit further includes a plurality of rotatable driving members. Each driving member is rotatably coupled to one actuator of the plurality of actuators such that rotation of each driving member independently axially moves one actuator of the plurality of actuators resulting in an axial movement of the corresponding driven member to actuate the end effector.

In embodiments, each actuator may include a cannulated cylindrical portion and an arm extending transversely from the cylindrical portion. The cylindrical portions are concentrically disposed with one another. Each arm may define a threaded passageway extending therethrough. Each driving member of the plurality of driving members may be threadingly coupled to a respective one of the threaded passageways of the plurality of actuators. Each driven member may further include a cannulated cylindrical portion having a proximal end and a distal end, a tab extending from the cylindrical portion of each driven member of the plurality of driven members, and a plurality of cables. The cannulated cylindrical portions may be concentrically disposed with one another. Each cable may be coupled between one tab and the end effector such that an axial movement of each driven member results in an actuation of the end effector via the plurality of cables.

In some aspects of the present disclosure, the instrument drive unit may further include at least one rotatable drive bar, and the surgical instrument may further include at least one drive gear disposed within the housing and coupled with the plurality of driven members. The at least one drive gear may be configured for non-rotatable connection to the at least one drive bar such that rotation of the at least one drive bar rotates the plurality of driven members via the at least one drive gear. The surgical instrument may further include a cylindrical body rotatably disposed within the housing and accommodating the plurality of driven members. The cylindrical body may have a proximal geared end in geared engagement with a first drive gear of the at least one drive gear and a distal geared end in geared engagement with a second drive gear of the at least one drive gear.

In embodiments, the surgical assembly may further include a threaded trocar shaft non-rotatably coupled with the instrument drive unit. The instrument drive unit may further include a nut threadingly engaged to the trocar shaft. The trocar shaft may axially move relative to the instrument drive unit and through the nut upon rotation of the nut. The trocar shaft may include a proximal end non-rotatably coupled with the instrument drive unit and a distal end having a lateral extension defining an opening therethrough configured for passage of the elongate body of the surgical instrument. The instrument drive unit may further include a drive gear in geared engagement with the nut and configured to drive the axial movement of the trocar shaft relative to the nut. The nut may have a geared outer surfaced in threaded engagement with the drive gear of the instrument drive unit. The trocar shaft may include an outer surface having a keyed portion non-rotatably engaged to a correspondingly shaped opening defined in the instrument drive unit. It is contemplated that each driving member may include a lead screw.

In another aspect of the present disclosure, an embodiment of a surgical instrument is provided. The surgical instrument is configured for coupling with an instrument drive unit that drives an actuation of the surgical instrument and operatively supports the surgical instrument. The surgical instrument includes a housing, an elongate body extending distally from the housing, an end effector extending distally from the elongate body, and a plurality of driven members rotatably disposed within the housing. The plurality of driven members is nested with one another. Each driven member is coupled to a respective cable that is attached to the end effector. The plurality of driven members is configured for engagement with an instrument drive unit.

In embodiments, each driven member may include a cannulated cylindrical portion, a tab extending from the cylindrical portion of each driven member, and a plurality of cables. The cylindrical portions may be nested with one another. Each cable may be coupled between one tab and the end effector such that an axial movement of each driven member of the plurality of driven members results in an actuation of the end effector via the plurality of cables.

The surgical instrument may further include at least one drive gear disposed within the housing and coupled with the plurality of driven members. Rotation of the at least one drive gear may rotate the plurality of driven members relative to the housing. The surgical instrument may further include a cylindrical body rotatably disposed within the housing and accommodating the plurality of driven members. The cylindrical body may have a proximal geared end in geared engagement with a first drive gear of the at least one drive gear and a distal geared end in geared engagement with a second drive gear of the at least one drive gear.

In yet another aspect of the present disclosure, an embodiment of an instrument drive unit is provided. The instrument drive unit is configured for driving an actuation of a surgical instrument and to operatively support the surgical instrument. The instrument drive unit includes a hub, a plurality of actuators, and a plurality of rotatable driving members. The hub defines a channel extending therethrough. The plurality of actuators is nested with one another and disposed through the channel of the hub. The plurality of rotatable driving members is rotatably coupled to the hub. Each driving member is rotatably coupled to one actuator of the plurality of actuators such that rotation of each driving member independently axially moves one actuator of the plurality of actuators.

In embodiments, each actuator may include a cannulated cylindrical portion and an arm extending transversely from the cylindrical portion. The cannulated cylindrical portions may be concentrically disposed with one another. The arm may define a threaded passageway therethrough. Each driving member may be threadingly coupled to a respective one of the threaded passageways of the plurality of actuators.

It is contemplated that the instrument drive unit may further include a threaded trocar shaft non-rotatably coupled with the hub, and a nut rotatably disposed with the hub and threadingly engaged to the trocar shaft. The trocar shaft may axially move relative to the hub and through the nut upon rotation of the nut. A rotatable drive gear may be in geared engagement with the nut and configured to drive the axial movement of the trocar shaft relative to the nut. In embodiments, each driving member may include a lead screw.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the present disclosure are described herein with reference to the accompanying drawings, wherein:

FIGS. 3A-3C illustrate an assembling of components of the surgical assembly shown in FIG. 2;

DETAILED DESCRIPTION

Figure 1:
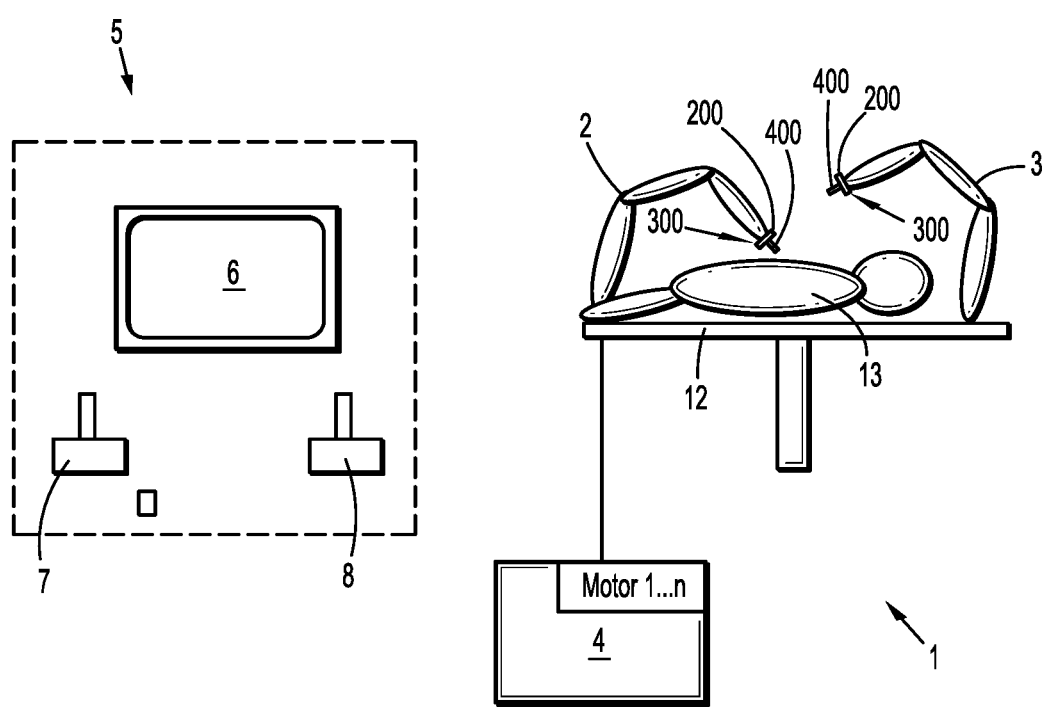
FIG. 1 is a schematic illustration of a surgical system in accordance with the present disclosure.
Figure 2:
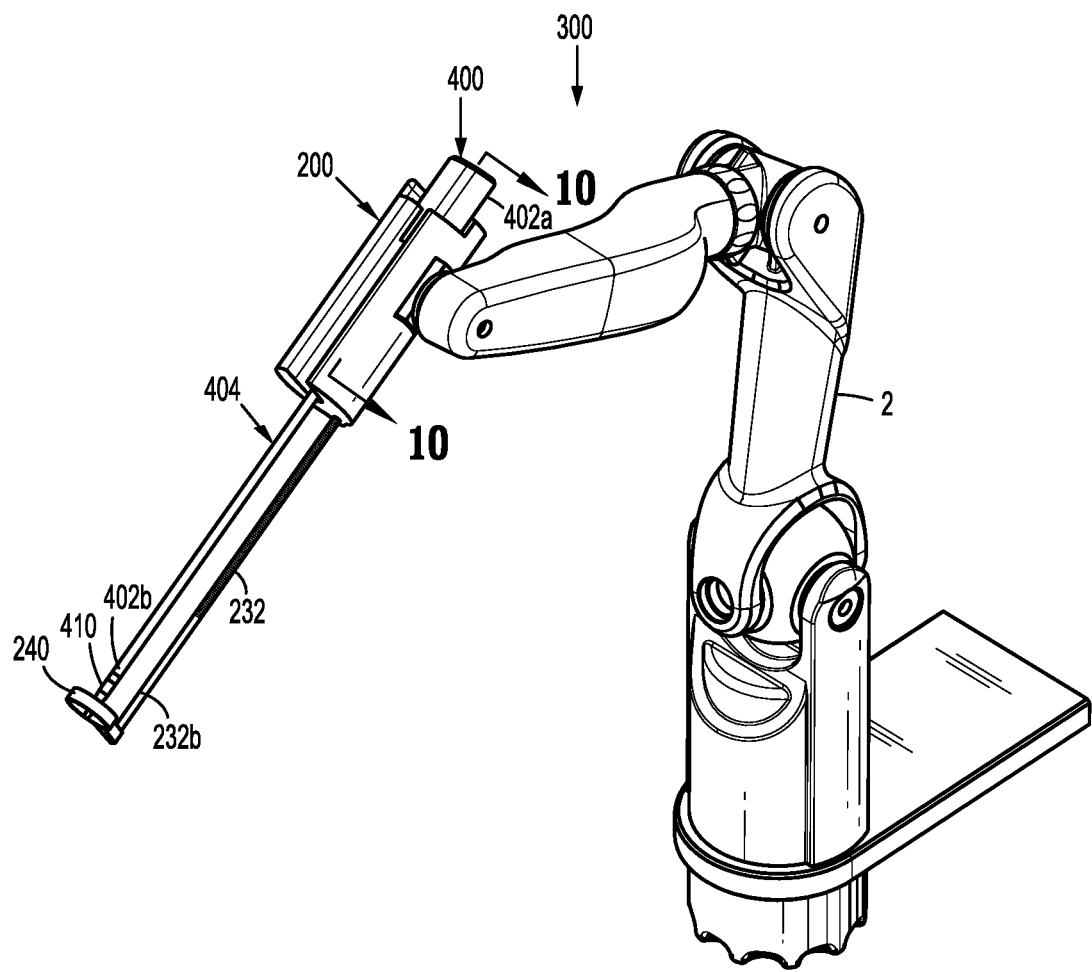
FIG. 2 is a perspective view of a surgical assembly in accordance with an embodiment of the present disclosure illustrated being attached to robot arms of a robotic surgical system.
Figure 4:
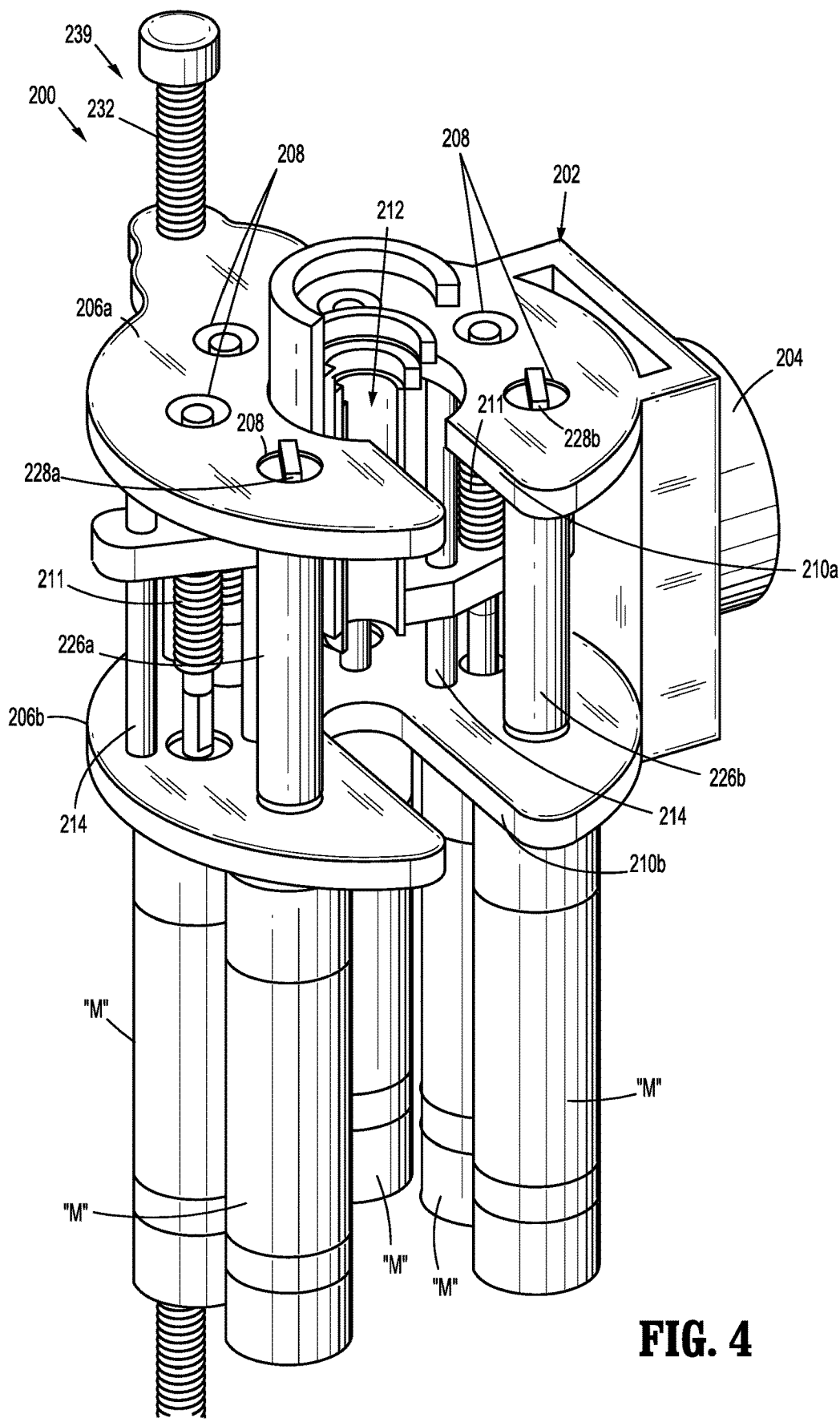
FIG. 4 is a cutaway view of an instrument drive unit of the surgical assembly shown in FIG. 2.
Figure 5:
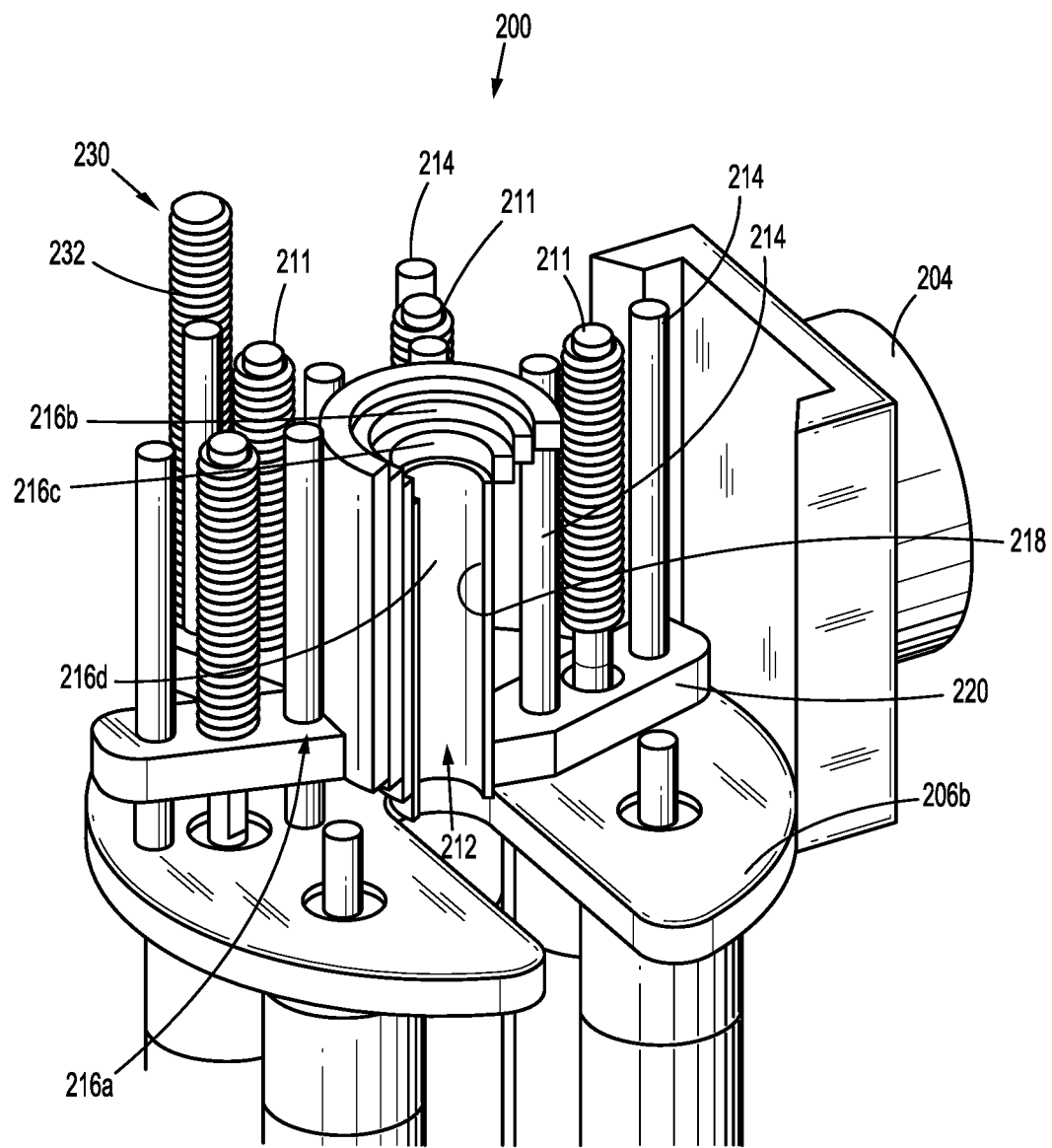
FIG. 5 is a front perspective view of the instrument drive unit shown in FIG. 4, with parts removed.

Embodiments of the presently disclosed surgical assembly including an instrument drive unit and a surgical instrument and methods thereof are described in detail with reference to the drawings, in which like reference numerals designate identical or corresponding elements in each of the several views. As used herein the term "distal" refers to that portion of the surgical instrument and/or instrument drive unit that is closer to the patient, while the term "proximal" refers to that portion of the surgical instrument and/or instrument drive unit that is farther from the patient.

Referring initially to FIG. 1, a surgical system, such as, for example, a robotic surgical system is shown generally as surgical system 1 and generally includes a plurality of robotic arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robotic arms 2, 3 in a first operating mode, as known in principle to a person skilled in the art.

Each of the robotic arms 2, 3 is composed of a plurality of members, which are connected through joints. System 1 also includes an instrument drive unit 200 connected to distal ends of each of robotic arms 2, 3. A surgical instrument 400 supporting an end effector 410 may be attached to instrument drive unit 200, in accordance with any one of several embodiments disclosed herein, as will be described in greater detail below.

Robotic arms 2, 3 may be driven by electric drives (not shown) that are connected to control device 4. Control device 4 (e.g., a computer) is set up to activate the drives, in particular by means of a computer program, in such a way that robotic arms 2, 3, their instrument drive units 200 and thus the surgical instrument 400 (including end effector 410) execute a desired movement according to a movement defined by means of manual input devices 7, 8. Control device 4 may also be set up in such a way that it regulates the movement of robotic arms 2, 3 and/or of the drives.

Surgical system 1 is configured for use on a patient 13 lying on a patient table 12 to be treated in a minimally invasive manner by means of an end effector. Surgical system 1 may also include more than two robotic arms 2, 3, the additional robotic arms likewise being connected to control device 4 and being telemanipulatable by means of operating console 5. A surgical instrument 400 (including end effector 410) may also be attached to the additional robotic arm.

Reference may be made to U.S. Pat. No. 8,828,023, filed on Nov. 3, 2011, entitled "Medical Workstation," the entire content of which is incorporated herein by reference, for a detailed discussion of the construction and operation of surgical system 1.

Control device 4 may control a plurality of motors (Motor 1 ... n) with each motor configured to drive a pushing or a pulling of a cable "C" extending between end effector 410 of surgical instrument 400 and a respective driven member 420a, 420b, 420c, 420d of surgical instrument 400, as described herein. In use, as cables "C" are pushed or pulled relative to end effector 410, cables "C" effect operation and/or movement of each end effector 410 of surgical instrument 400. It is contemplated that control device 4 coordinates the activation of the various motors (Motor 1 ... n) to coordinate a pushing or a pulling motion of a respective cable in order to coordinate an operation and/or movement of a respective end effector 410. In embodiments, each motor can be configured to actuate a drive rod or a lever arm to effect operation and/or movement of each end effector of surgical instrument 400.

Turning to FIGS. 2-12, surgical system 1 includes a surgical assembly 300, which includes robotic arm 2, an instrument drive unit 200 connected to robotic arm 2, and surgical instrument 400 coupled with or to instrument drive unit 200. As shown in FIGS. 3A-3C, surgical instrument 400 can be top loaded into instrument drive unit 200. Specifically, to load surgical instrument 400 into instrument drive unit 200, surgical instrument 400 is translated transverse to instrument drive unit 200 (surgical instrument 400 is slid into a longitudinal slot/channel 201 of instrument drive unit 200), in a direction indicated by arrow "A" in FIG. 3A, into instrument drive unit 200, and then translated axially, in a direction indicated by arrow "B" in FIG. 3B, to engage various components of surgical instrument 400 with corresponding components of instrument drive unit 200, as described in greater detail below.

Instrument drive unit 200 is configured for driving an actuation of end effector 410 of surgical instrument 400 and to operatively support surgical instrument 400 therein. Instrument drive unit 200 transfers power and actuation forces from motors "M" (FIG. 4) to surgical instrument 400 to ultimately drive movement of cables "C" that are attached to end effector 410. Instrument drive unit 200 includes a plurality of driving members, such as, for example, lead screws 211, attached to a respective motor "M" such that lead screws 211 are independently rotatable with respect to one another. Lead screws 211, in combination and cooperation with a plurality of actuators 216a, 216b, 216c, 216d, convert rotational movement into axial movement to actuate or carry out certain functions of end effector 410.

With reference to FIGS. 4-7, instrument drive unit 200 includes a hub or platform 202 for supporting various components of instrument drive unit 200 and for connecting to robotic arm 2 of surgical assembly 300. Hub 202 includes a connecting member or disc-shaped protrusion 204 configured for rotatable coupling to a correspondingly shaped socket (not shown) defined in robotic arm 2 of surgical assembly 300. The socket defined in robotic arm 2 may contain electrical components to transmit power/signals to/from instrument drive unit 200 and robotic arm 2. Hub 202 further includes a first plate 206a and a second plate 206b, spaced from the first plate 206a and in coaxial alignment therewith. Plates 206a, 206b are each fixed relative to connecting member 204. Each plate 206a, 206b defines a plurality of channels 208 extending therethrough. First plate 206a further defines a first notch or channel 210a having a key shaped configuration, and second plate 206b defines a second notch or channel 210b having an elongated configuration such that notches 210a, 210b together define a central channel or passageway 212 therebetween. In some embodiments, notches 210a, 210b can be variously configured, such as, for example, in any suitable shape or configuration. Passageway 212 is configured for disposal of a plurality of actuators 216a, 216b, 216c, 216d of instrument drive unit 200, as described herein. Channels 208 are disposed about passageway 212 and are each configured for disposal of either one of lead screws 211 or actuators 216a, 216b, 216c, 216d. Hub 202 further includes a plurality of guiderails 214 extending between first and second plates 206a, 206b for actuators 216a, 216b, 216c, 216d to slide along.

As previously mentioned, instrument drive unit 200 includes a plurality of actuators 216a, 216b, 216c, 216d. Actuators 216a, 216b, 216c, 216d are nested with one another and disposed through passageway 212 of hub 202. Each actuator 216a, 216b, 216c, 216d is slidingly disposed with at least one guiderail 214 and a respective lead screw 211. Each actuator 216a, 216b, 216c, 216d includes a cannulated cylindrical portion 218 disposed within passageway 212 and an arm or tongue 220 extending transversely or perpendicularly from cylindrical portion 218. Cylindrical portions 218 successively decrease in diameter from an outermost actuator 216a toward an innermost actuator 216d. Cylindrical portions 218 are cannulated such that cylindrical portions 218 can be concentrically disposed with one another, or nested, and so that surgical instrument 400 can be inserted therethrough.

Tongue 220 of each actuator 216a, 216b, 216c, 216d can be integrally connected to or monolithically formed with a distal end of cylindrical portion 218. Tongue 220 defines a first channel 222a having a guiderail 214 disposed therein, a second channel 222b having another guiderail 214 disposed therein, and a threaded passageway 224 disposed between channels 222a, 222b and threadingly coupled with a respective lead screw 211. In this way, a rotation of one of lead screws 211 drives an axial movement of a respective actuator 216a, 216b, 216c, 216d along guiderails 214 and between first and second plates 206a, 206b of hub 202 independently with respect to one another. The axial movement of actuators 216a, 216b, 216c, 216d drives an axial movement of a respective driven member 420a, 420b, 420c, 420d of surgical instrument 400 to actuate functions of end effector 410, as described in greater detail below.

Instrument drive unit 200 further includes a first rotatable drive bar 226a and a second rotatable drive bar 226b each rotatably supported between plates 206a, 206b of hub 202. A distal end of each drive bar 226a, 226b is coupled to a respective motor "M" for driving a rotation of each drive bar 226a, 226b. A proximal end of each drive bar 226a, 226b includes a coupling feature, such as, for example, a flat-head 228a, 228b configured for non-rotatable engagement with a correspondingly shaped coupling feature 418a, 418b of a drive gear 416a, 416b of surgical instrument 400 (FIG. 12), respectively, to drive a rotation of an elongate body 404 and end effector 410 of surgical instrument 400, as described in further detail below.

As illustrated in FIGS. 4-8, instrument drive unit 200 further includes a trocar assembly 230 for selectively positioning end effector 410 of surgical instrument 400 relative to a target surgical site. Trocar assembly 230 includes a threaded trocar shaft 232 having a proximal end 232a and a distal end 232b. Proximal end 232a of trocar shaft 232 is non-rotatably coupled with plates 206a, 206b of hub 202. With specific reference to FIG. 8, an outer surface 234 of at least proximal end 232a of trocar shaft 232 has a keyed portion 236 non-rotatably engaged to a correspondingly shaped opening 238 defined in hub 202. Distal end 232b of trocar shaft 232 has a lateral extension or ring 240 (FIGS. 2, 9A, and 9B) defining an opening 242 therethrough configured for passage of elongated body 204 of surgical instrument 400. Ring 240 can be selectively positioned on an operating surface, such as, for example, skin of a patient, such that end effector 410 can be guided toward a target surgical location of a patient.

Figure 6:
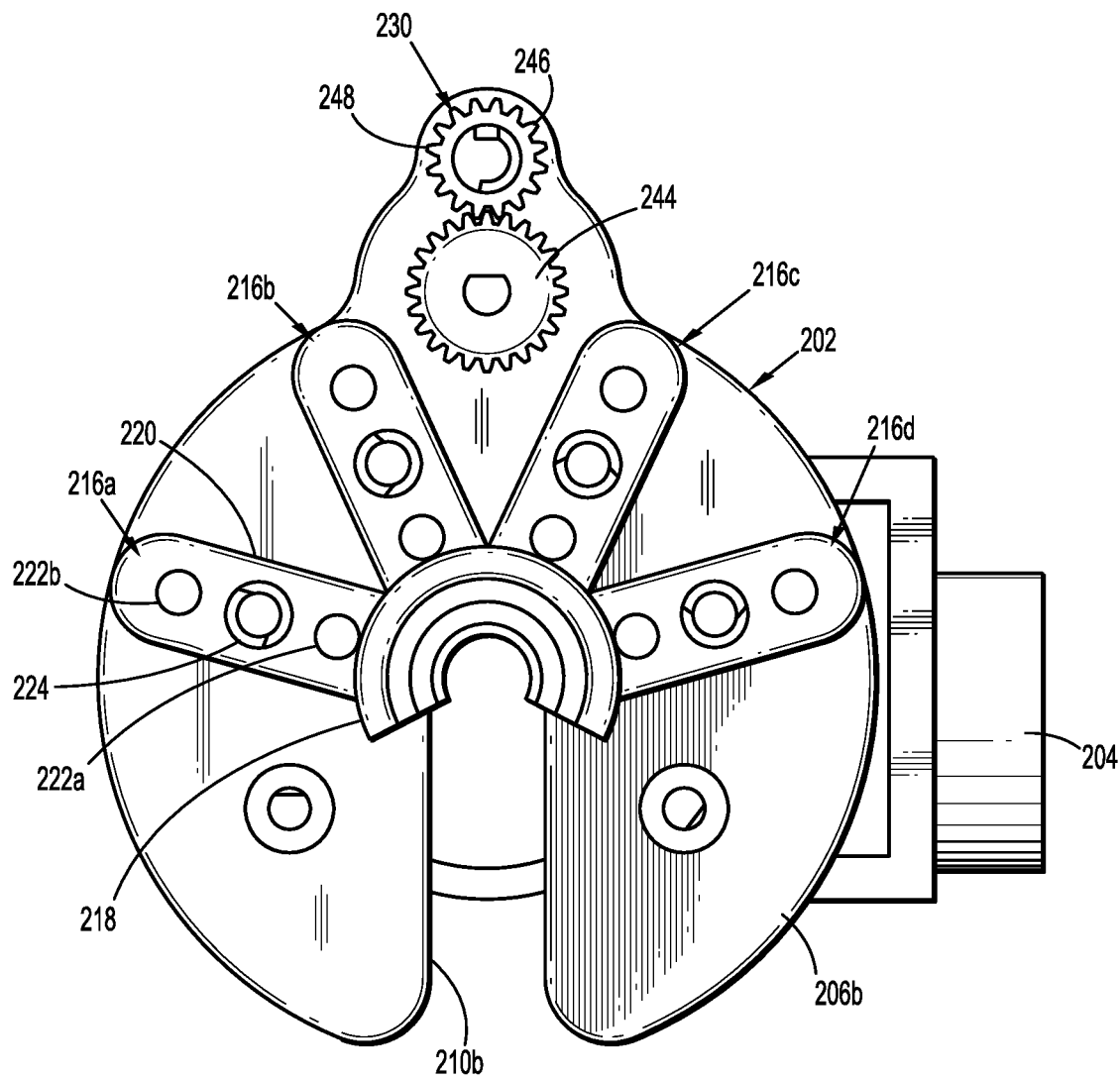
FIG. 6 is a top view of the instrument drive unit shown in FIG. 5.
Figure 7:
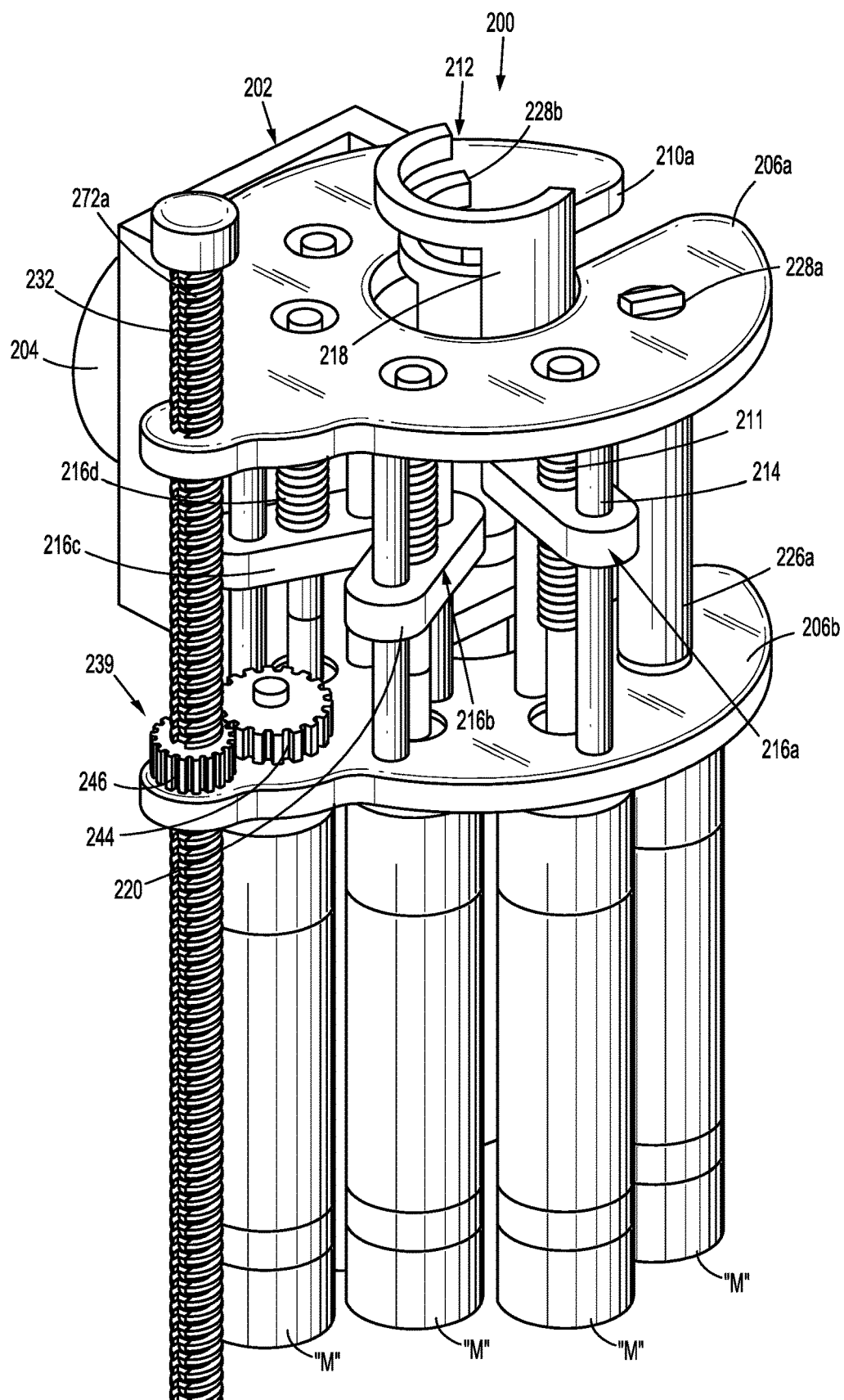
FIG. 7 is a rear perspective view of the instrument drive unit shown in FIG. 4.
Figure 8:
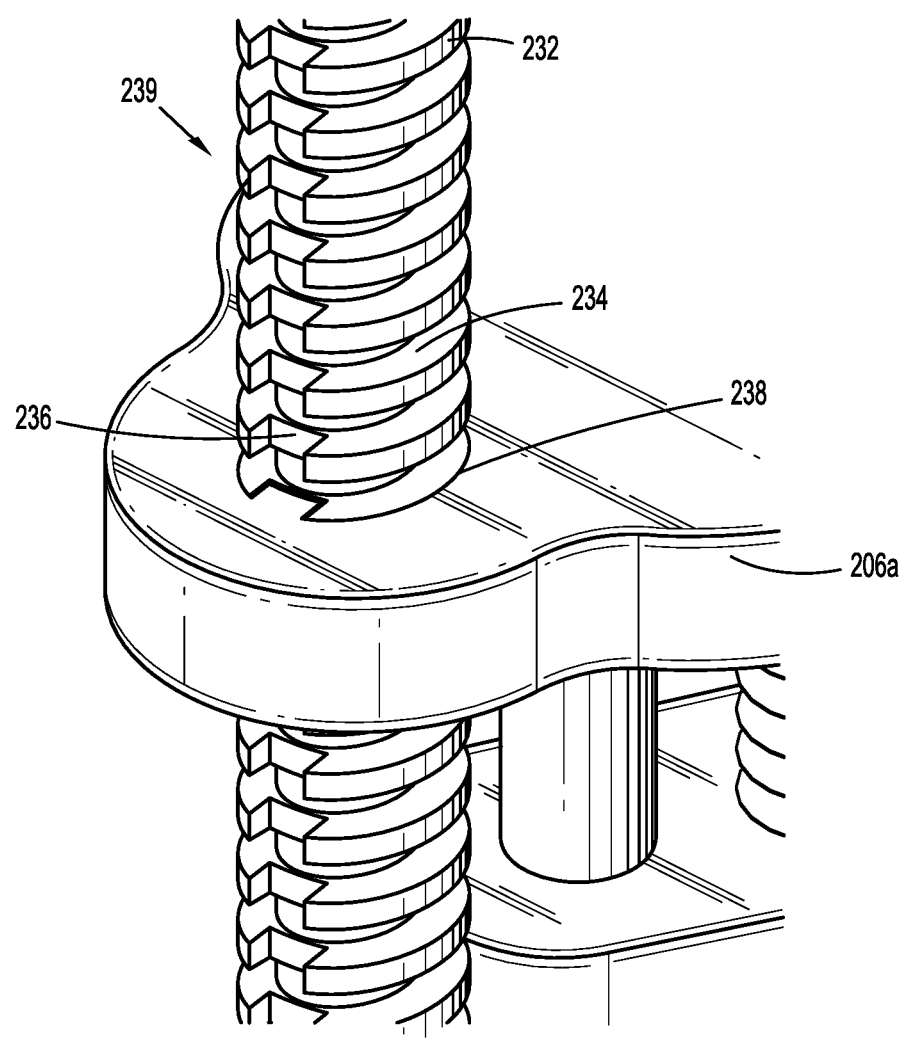
FIG. 8 is an expanded view of a trocar assembly of the instrument drive unit shown in FIG. 7.
Figure 9:
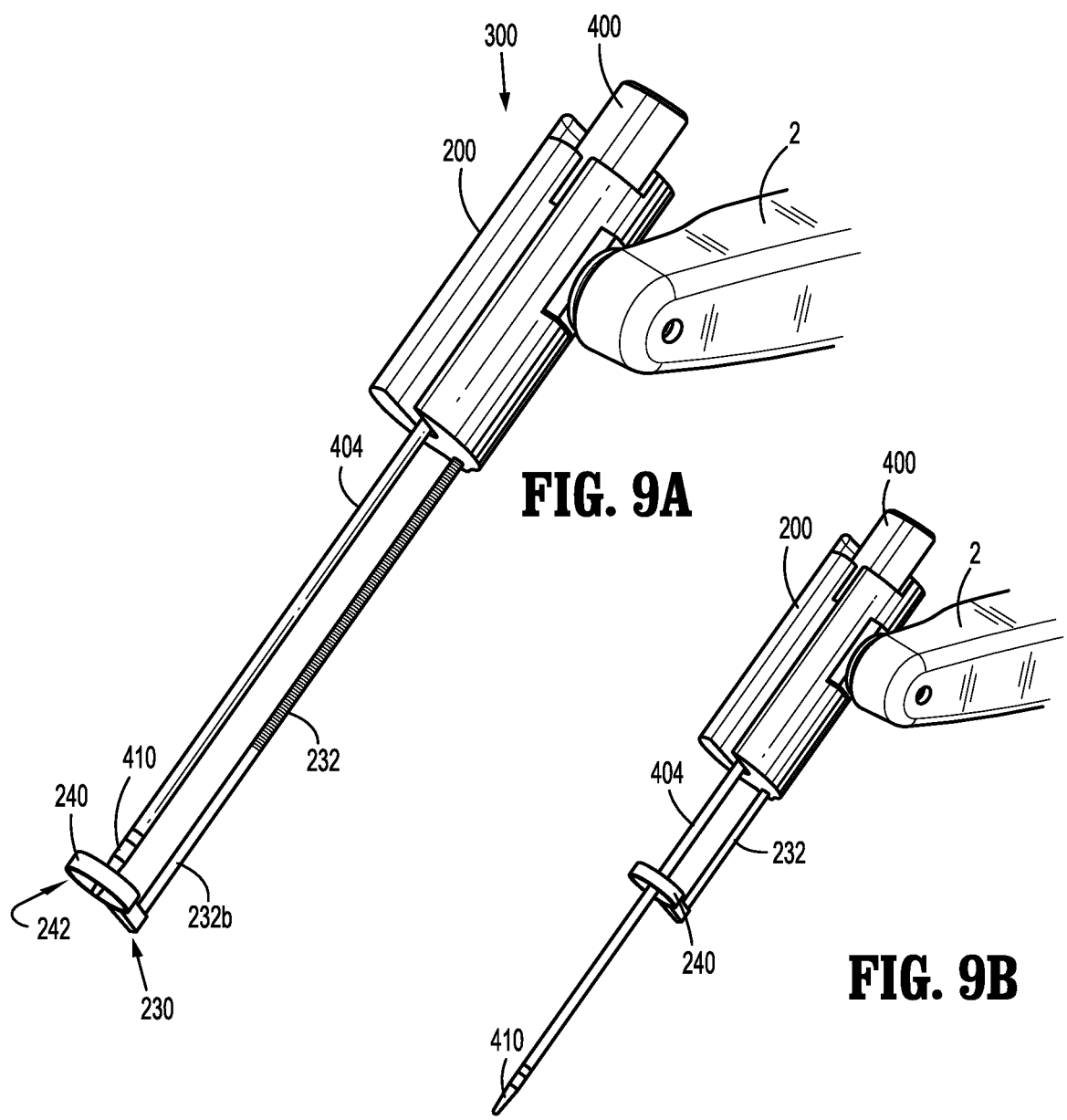
FIGS. 9A and 9B illustrate a movement of the trocar assembly shown in FIG. 8 between alternate positions relative to the surgical instrument shown in FIG. 2.
Figure 10:
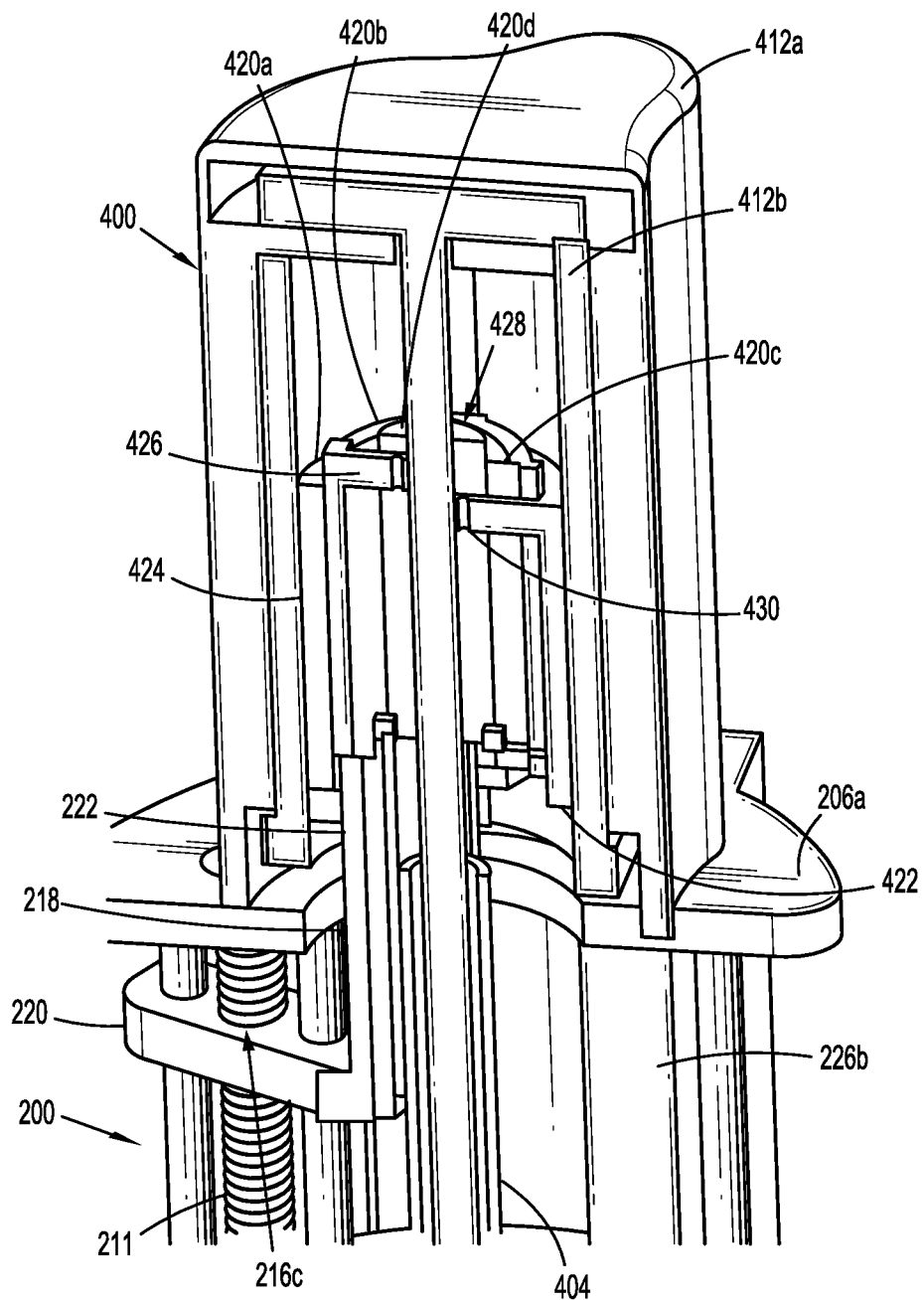
FIG. 10 is a cross sectional view, taken along lines 10-10 in FIG. 2, of the surgical instrument and the instrument drive unit of the surgical assembly.
Figure 11:
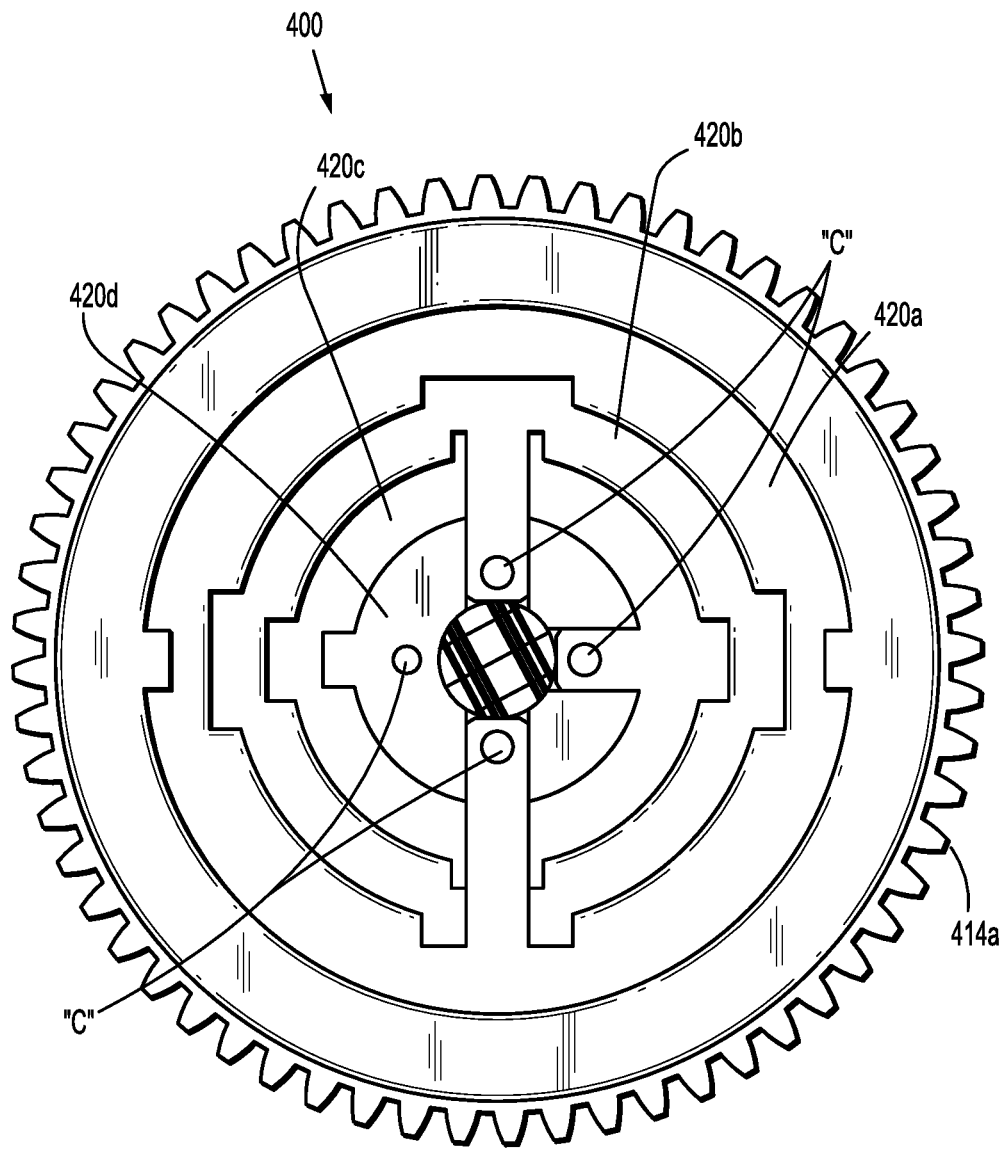
FIG. 11 is a top view of an inner housing of the surgical instrument shown in FIG. 10.

With continued reference to FIGS. 6 and 7, trocar assembly 230 further includes a gear, such as, for example, a spur gear 244, and a nut 246. Spur gear 244 is rotatably supported on plate 206b and coupled to a motor "M" for driving a rotation of spur gear 244. Nut 246 is supported on plate 206b and has a geared outer surface 248 in geared engagement with spur gear 244, such that rotation of spur gear 244 drives a rotation of nut 246. Nut 246 includes an internal thread form (not shown) having trocar shaft 232 threadingly engaged thereto for translating trocar shaft 232 therealong and therethrough.

In use, trocar shaft 232 is moved between a pre-operative position, as shown in FIG. 9A, and an operative position, as shown in FIG. 9B. In the pre-operative position, ring 240 and end effector 410 are coplanar. In the operative position, ring 240 is located proximal to end effector 410. To move between the pre-operative and operative positions, spur gear 244 is rotated via a motor "M," which results in a concomitant rotation of nut 246, driving an axial movement of trocar shaft 232 relative to and along hub 202.

Surgical instrument 400 will now be described in detail with reference to FIGS. 2 and 10-13. Surgical instrument 400 generally has a proximal end portion 402a configured to be engaged with instrument drive unit 200 and a distal end portion 402b having an end effector 410 extending therefrom. Surgical instrument 400 includes an outer housing 412a and an inner housing or cylindrical body 412b disposed within outer housing 412a and rotatable relative thereto. Surgical instrument 400 further includes an elongate body or tube 404 engaged with inner housing 412b and extending distally therefrom. End effector 410 extends distally from distal end 402b of elongate body 404 and is configured for performing a plurality of surgical functions.

Outer housing 412b is configured for fixed engagement with instrument drive unit 200. Inner housing 412b houses or accommodates a plurality of driven members 420a, 420b, 420c, 420d rotatably disposed therein. Inner housing 412b has a proximal geared end 414a and a distal geared end 414b. Surgical instrument 400 further includes a first drive gear 416a and a second drive gear 416b each disposed within outer housing 412a and coupled with the plurality of driven members 420a, 420b, 420c, 420d via the proximal and distal geared ends 414a, 414b of inner housing 412b, respectively. First drive gear 416a includes a socket 418a having a rectangular shape (or non-circular) configured for non-rotatable connection with flat-head 228a of first drive bar 226a of instrument drive unit 200. Second drive gear 416b includes a socket 418b having a rectangular shape (or non-circular) configured for non-rotatable connection to flat-head 228b of second drive bar 226b of instrument drive unit 200.

Figure 12:
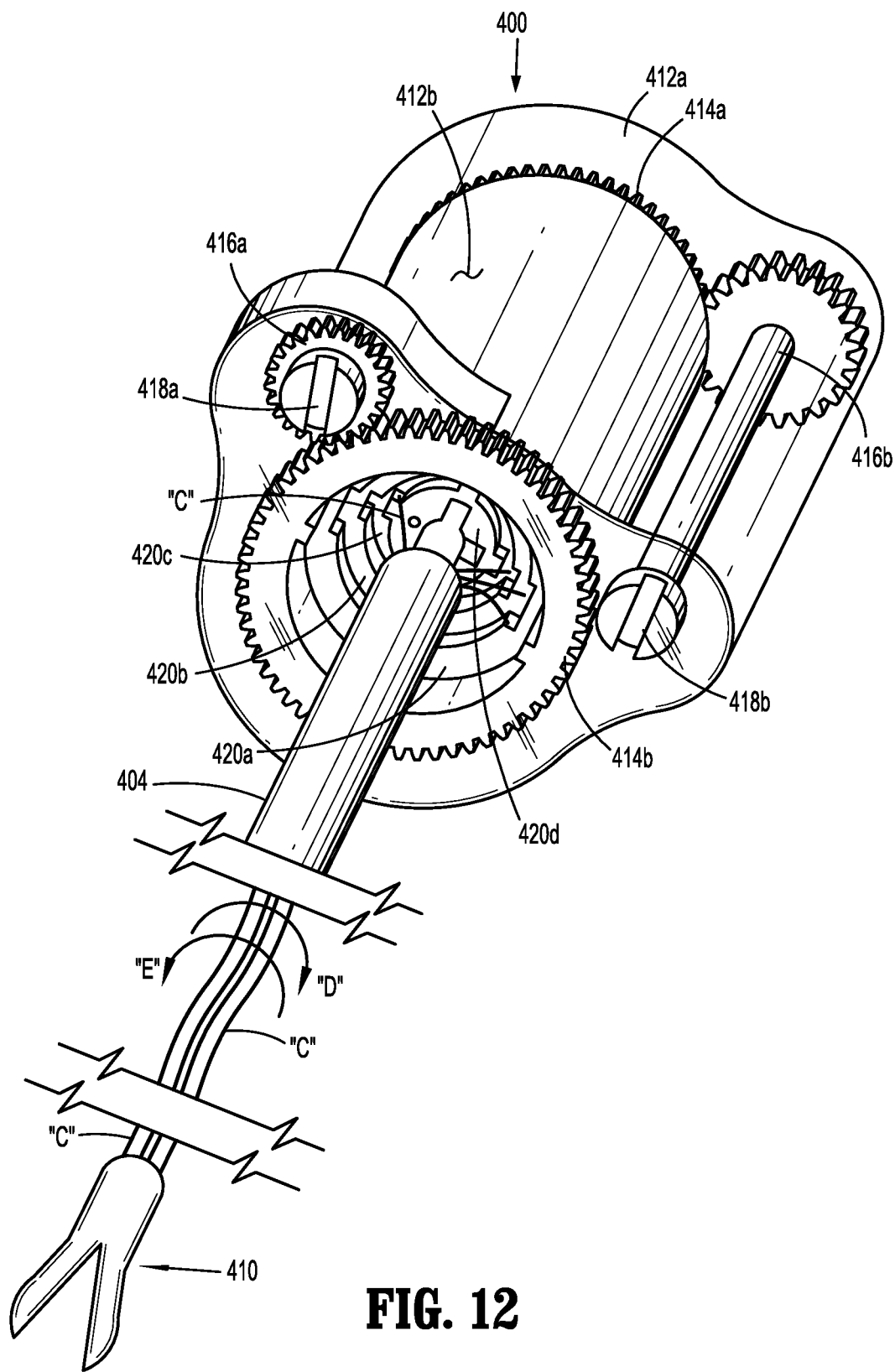
FIG. 12 is a perspective view, in part phantom, of the surgical instrument shown in FIG. 2.

In use, a rotation of drive bars 226a, 226b of instrument drive unit 200 rotates inner housing 412b relative to outer housing 412a via distal geared end 414b, which results in a concomitant rotation of elongate tube 404 and end effector 410, in directions indicated by arrows "D" or "E" in FIG. 12. That is, as inner housing 412b rotates, all of driven members 420a, 420b, 420c, 420d rotate therewith such that cables "C," that are attached with and extend from driven members 420a, 420b, 420c, 420d, do not get entangled with one another during rotation of end effector 410. Further, proximal geared end 414a, second drive gear 416b, and socket 418b may be actuated to provide additional torque through elongate tube 404 for certain instruments (e.g., a stapler) that may require an additional driving force.

As mentioned above, surgical instrument 400 includes a plurality of driven members 420a, 420b, 420c, 420d corresponding to actuators 216a, 216b, 216c, 216d of instrument drive unit 200. Driven member 420a, 420b, 420c, 420d are disposed within inner housing 412b and are rotatable relative to and within inner housing 412b. Driven members 420a, 420b, 420c, 420d are nested with one another, similar to actuators 216a, 216b, 216c, 216d of instrument drive unit 200. Each driven member 420a, 420b, 420c, 420d is coupled to a respective cable "C" that is attached to end effector 410. Cables "C" extend from driven members 420a, 420b, 420c, 420d, through elongate body 404 of surgical instrument 400, and to end effector 410. Therefore, a movement or translation of each driven member 420a, 420b, 420c, 420d results in a concomitant movement or translation of a respective cable "C" to carry out a function of end effector 410, such as, for example, an opening and closing of jaws of end effector 410, an actuation of just one jaw, a pivoting of the jaws, a deployment of a staple from end effector 410, etc.

Each driven member 420a, 420b, 420c, 420d has a distal end 422 configured for engagement with one corresponding actuator 216a, 216b, 216c, 216d of instrument drive unit 200. Accordingly, with surgical instrument 400 disposed within instrument drive unit 200, an axial movement of one actuator 216a, 216b, 216c, 216d of instrument drive unit 200, via rotation of a respective lead screw 211, results in an axial movement of a corresponding driven member 420a, 420b, 420c, 420d of surgical instrument 400. It is contemplated that distal end 422 of each driven member 420a, 420b, 420c, 420d can be engaged with a proximal end 222 of each actuator 216a, 216b, 216c, 216d via various fastening engagements, such as, for example, bayonet-type engagement, snap-fit engagement, frictional engagement, or rotate and lock engagements.

Each driven member 420a, 420b, 420c, 420d includes a cannulated cylindrical portion 424 and a tab 426 extending from each cylindrical portion 424 toward a central passageway 428 defined through cylindrical portions 424. Cylindrical portions 424 have varying diameters so that cylindrical portions 424 can be concentrically disposed within or nested with one another. Each tab 426 defines a slot 430 therein having one cable "C" (FIG. 11) fixedly secured therein. In some embodiments, each cable "C" is fixedly engaged to tab 426 via various fastening engagements, such as, for example, snap-fit engagement, frictional engagement, adhesives, and/or various fasteners.

In operation, surgical instrument 400 is inserted within instrument drive unit 200 to engage each actuator 216a, 216b, 216c, 216d of instrument drive unit 200 with a corresponding driven member 420a, 420b, 420c, 420d of surgical instrument 400. With actuators 216a, 216b, 216c, 216d engaged with respective driven members 420a, 420b, 420c, 420d, an axial or linear movement of actuators 216a, 216b, 216c, 216d, caused by a rotation of lead screws 211, drives an axial movement of a respective driven member 420a, 420b, 420c, 420d due to the engagement between actuators 216a, 216b, 216c, 216d and respective driven members 420a, 420b, 420c, 420d. An axial movement of a driven member 420a, 420b, 420c, 420d results in a translation of a respective cable "C" in either a proximal or distal direction, through elongate body 404 of surgical instrument 404, to actuate functions of end effector 410, as described above.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An instrument drive unit configured for driving an actuation of a surgical instrument and to operatively support the surgical instrument, the instrument drive unit comprising:
    a hub defining a channel extending therethrough;
    a plurality of actuators nested with one another and disposed through the channel; and
    a plurality of driving members rotatably coupled to the hub, wherein each driving member of the plurality of driving members is rotatably coupled to one actuator of the plurality of actuators such that rotation of each driving member of the plurality of driving members independently axially moves one actuator of the plurality of actuators.

2. The instrument drive unit according to claim 1, wherein each actuator of the plurality of actuators includes a cannulated cylindrical portion and an arm extending transversely from the cylindrical portion.

3. The instrument drive unit according to claim 2, wherein the cylindrical portions are concentrically disposed with one another.

4. The instrument drive unit according to claim 2, wherein the arm defines a threaded passageway therethrough, and wherein each driving member of the plurality of driving members is threadingly coupled to a respective one of the threaded passageways of the plurality of actuators.

5. The instrument drive unit according to claim 1, further comprising:
    a threaded trocar shaft non-rotatably coupled with the hub; and
    a nut rotatably disposed with the hub and threadingly engaged to the trocar shaft, wherein the trocar shaft axially moves relative to the hub and through the nut upon rotation of the nut.

6. The instrument drive unit according to claim 5, further comprising a rotatable drive gear in geared engagement with the nut and configured to drive the axial movement of the trocar shaft relative to the nut.

7. The instrument drive unit according to claim 1, wherein each driving member of the plurality of driving members includes a lead screw operably coupled to a respective actuator, such that each actuator of the plurality of actuators moves axially in response to a rotation of the respective lead screw.

8. The instrument drive unit according to claim 7, wherein the plurality of lead screws extend in side-by-side and parallel relation with the plurality of actuators.

9. The instrument drive unit according to claim 1, wherein each actuator of the plurality of actuators has a proximal end configured to engage a distal end of one corresponding driven member of a plurality of driven members of the surgical instrument.

10. The instrument drive unit according to claim 1, wherein the plurality of actuators defines a longitudinally-extending central channel configured for receipt of an elongate body of the surgical instrument.

11. An instrument drive unit of a surgical robotic system, the instrument drive unit comprising:
    a plurality of drive motors;
    a plurality of driving members coupled to the respective drive motors and configured to be rotated by the drive motors; and
    a plurality of longitudinally-extending actuators concentrically disposed with one another, wherein each driving member of the plurality of driving members is coupled to one actuator of the plurality of actuators such that rotation of each driving member of the plurality of driving members independently axially moves one actuator of the plurality of actuators.

12. The instrument drive unit according to claim 11, wherein the plurality of actuators defines a longitudinally-extending central channel configured for receipt, in a distal direction, of a surgical instrument.

13. The instrument drive unit according to claim 12, further comprising a proximal plate, and a distal plate distally spaced from the proximal plate, wherein each of the proximal and distal plates defines a lateral notch configured for lateral receipt of the surgical instrument.

14. The instrument drive unit according to claim 11, wherein each actuator of the plurality of actuators includes a cannulated cylindrical portion and an arm extending transversely from the cylindrical portion.

15. The instrument drive unit according to claim 14, wherein the cylindrical portions are concentrically disposed with one another.

16. The instrument drive unit according to claim 14, wherein the arm defines a threaded passageway therethrough, and wherein each driving member of the plurality of driving members is threadingly coupled to a respective one of the threaded passageways of the plurality of actuators.

17. The instrument drive unit according to claim 11, further comprising:
    a hub supporting the plurality of drive motors;
    a threaded trocar shaft non-rotatably coupled with the hub; and
    a nut rotatably disposed with the hub and threadingly engaged to the trocar shaft, wherein the trocar shaft axially moves relative to the hub and through the nut upon rotation of the nut.

18. The instrument drive unit according to claim 11, wherein each driving member of the plurality of driving members includes a lead screw operably coupled to a respective actuator, such that each actuator of the plurality of actuators moves axially in response to a rotation of the respective lead screw.

19. The instrument drive unit according to claim 18, wherein the lead screws extend in side-by-side and parallel relation with the plurality of actuators.

20. The instrument drive unit according to claim 11, wherein each actuator of the plurality of actuators has a proximal end configured to engage a distal end of one corresponding driven member of a plurality of driven members of the surgical instrument.

* * * * *